United States Patent
Mennen

(10) Patent No.: US 9,815,800 B2
(45) Date of Patent: Nov. 14, 2017

(54) INTEGRATED PRODUCTION OF UREA AND MELAMINE

(71) Applicant: Stamicarbon B.V., Sittard (NL)

(72) Inventor: Johannes Henricus Mennen, Sittard (NL)

(73) Assignee: Stamicarbon B.V., Sittard (NL)

( * ) Notice: Subject to any disclaimer, the term of this patent is extended or adjusted under 35 U.S.C. 154(b) by 0 days.

(21) Appl. No.: 15/106,140

(22) PCT Filed: Dec. 16, 2014

(86) PCT No.: PCT/NL2014/050863
§ 371 (c)(1),
(2) Date: Jun. 17, 2016

(87) PCT Pub. No.: WO2015/093942
PCT Pub. Date: Jun. 25, 2015

(65) Prior Publication Data
US 2016/0318883 A1    Nov. 3, 2016

(30) Foreign Application Priority Data
Dec. 17, 2013    (EP) .................................... 13197863

(51) Int. Cl.
C07D 251/60    (2006.01)
C07D 251/62    (2006.01)
C07C 273/12    (2006.01)
B01J 19/24    (2006.01)
B01J 3/04    (2006.01)
B01J 4/00    (2006.01)
B01J 10/00    (2006.01)

(52) U.S. Cl.
CPC .......... *C07D 251/60* (2013.01); *B01J 19/245* (2013.01); *C07C 273/12* (2013.01); *B01J 2219/00103* (2013.01); *B01J 2219/24* (2013.01)

(58) Field of Classification Search
CPC .. C07D 251/60; C07D 251/62; C07C 273/12; B01J 19/245
USPC .................................. 544/201, 203; 422/255
See application file for complete search history.

(56) References Cited

U.S. PATENT DOCUMENTS

| 7,893,298 B2 | 2/2011 | Mennen et al. |
| 8,721,975 B2 * | 5/2014 | Filippi ................ B01J 19/0013 165/157 |
| 2006/0052637 A1 | 3/2006 | Porro |
| 2009/0220396 A1 * | 9/2009 | Filippi ................ B01J 19/0013 422/201 |

FOREIGN PATENT DOCUMENTS

| EP | 1 918 274 | 5/2008 |
| WO | WO-98/08808 | 3/1998 |
| WO | WO-2008/052640 | 5/2008 |

OTHER PUBLICATIONS

International Search Report for PCT/NL2014/050863, dated Apr. 2, 2015, 3 pages.

* cited by examiner

*Primary Examiner* — Venkataraman Balasubramanian
(74) *Attorney, Agent, or Firm* — Morrison & Foerster LLP

(57) ABSTRACT

Disclosed is a process for the integrated production of urea and melamine. A urea production zone produces a urea synthesis stream comprising urea, water and ammonium carbamate. This stream is subjected to processing, preferably involving stripping, so as to separate an aqueous urea stream from residual dissociated carbamate vapor comprising ammonia, carbon dioxide, and water. The urea is fed to a melamine synthesis zone and subjected to melamine forming conditions so as to form melamine and off-gas comprising carbon dioxide and ammonia. The dissociated carbamate vapor and the melamine off-gas are subjected to combined condensation so as to form a dilute melamine off-gas condensate.

3 Claims, 11 Drawing Sheets

INTEGRATED PRODUCTION OF UREA AND MELAMINE

CROSS-REFERENCE TO RELATED APPLICATIONS

This application is the national phase of PCT application PCT/NL2014/050863 having an international filing date of 16 Dec. 2014, which claims benefit of European patent application No. 13197863.7 filed 17 Dec. 2013. The contents of the above patent applications are incorporated by reference herein in their entirety.

FIELD OF THE INVENTION

The invention relates to the integration of urea and melamine production, in particular of urea and melamine produced according high-pressure liquid phase melamine technology. The invention also pertains to methods for revamping pre-existing urea and melamine plants.

BACKGROUND OF THE INVENTION

The integration of urea and melamine production has long been known. Melamine is thereby produced from urea, according the following reaction:

$$6(NH_2)_2CO \rightarrow C_3H_6N_6 + 6NH_3 + 3CO_2$$

Interestingly, ammonia and carbon dioxide result from this process in precisely in the stoichiometric ratio from which these substances form urea.

The latter is generally presented in the form of two consecutive reaction steps. In the first step, ammonium carbamate being formed according to the exothermic reaction:

$$2NH_3 + CO_2 \rightarrow H_2N\text{—}CO\text{—}ONH_4$$

Thereafter the formed ammonium carbamate is dehydrated in the second step to give urea according to the endothermic equilibrium reaction:

$$H_2N\text{—}CO\text{—}ONH_4 \leftrightarrow H_2N\text{—}CO\text{—}NH_2 + H_2O$$

In the art, urea plants are generally filled with starting materials on the basis of an excess of ammonia (i.e. above the 2:1 stoichiometric ratio). These reactants are subjected to a pressure between 12 and 40 MPa and a temperature between 150° C. and 250° C. in a urea synthesis zone.

In the integrated production of urea and melamine, urea produced in a urea synthesis zone is sent to a melamine synthesis zone. The carbon dioxide and ammonia off-gas resulting from the melamine production is, in turn, recirculated as a starting material for use in the urea synthesis zone.

It will be understood that, irrespective of the excess of ammonia introduced, the reactants are drawn from the synthesis zone in not more than a 2:1 ratio, and the off-gas from the melamine synthesis thus reintroduces the urea-forming reactants in the same ratio. Thus, the ammonia to carbon dioxide ratio in the entire urea and melamine synthesis and recirculation loop remains the same.

The integrated production can take place in an integrated plant, having urea and melamine synthesis zones. More typically, however, the melamine and urea synthesis zones are comprised in separate plants for the production of urea and melamine, which plants are coupled using the appropriate flow lines so as to realize the aforementioned integration.

A typical urea plant is a urea stripping plant. Therein, the decomposition of the ammonium carbamate that has not been converted into urea and the expulsion of the usual ammonia excess largely takes place at a pressure that is essentially almost equal to or lower than the pressure in the synthesis reactor. This decomposition and expulsion take place in one or more stripper(s) installed downstream of the reactor, possibly with the aid of a stripping gas such as, for example, carbon dioxide or ammonia, and with the addition of heat. The gas stream leaving a stripper contains ammonia and carbon dioxide which are condensed in a high-pressure condenser, operating at essentially equal pressure to the pressure in the stripper and then returned to the urea synthesis zone.

In a urea stripping plant the synthesis zone is operated at a temperature of 160-240° C. and preferably at a temperature of 170-220° C. The pressure in the synthesis reactor is 12-21 MPa, preferably 12.5-20 MPa. The ammonia to carbon dioxide molar ratio (N/C ratio) in the urea synthesis zone of a stripping plant lies usually in between 2.2 and 5 and preferably between 2.5 and 4.5 mol/mol. The synthesis zone can be carried out in a single reactor or in a plurality of reactors arranged in parallel or series.

After the stripping treatment, the pressure of the stripped urea solution is reduced in a urea recovery section (or recirculation section, as from this section carbamate is recirculated). In a recovery section the non-converted ammonia and carbon dioxide in the urea solution is separated from the urea and water solution. A recovery section comprises usually a heater, one or more liquid/gas separation sections and one or more condensation sections. The urea solution entering a recovery section is heated to vaporize the volatile components ammonia and carbon dioxide from that solution. The heating agent used in the heater is usually steam. The formed vapor in said heater is separated from the aqueous urea solution in the liquid/gas after which said vapor is condensed in the condenser to form a carbamate solution. The released condensation heat is usually dissipated in cooling water. The formed carbamate solution in that recovery section operated at a lower pressure than the pressure in the synthesis section is preferably returned to the urea synthesis section operating at synthesis pressure. The recovery section is generally a single section or can be a plurality of recovery sections arranged in series.

In a urea stripping plant operating with carbon dioxide as a stripping gas, it is normally advantageous to introduce substantially all of the carbon dioxide into the synthesis loop via the stripper. In the event of the integrated production of urea and melamine, however, part of the carbon dioxide feed is determined by the recirculation of the off-gas of the melamine production. Since this off-gas contains both carbon dioxide and ammonia, it is less suitable to be used as a stripping medium, as using it would not result in a decrease of the partial pressure of only one if the components in the liquid phase.

With part of the carbon dioxide reactants thus being introduced elsewhere into the urea synthesis section, the carbon dioxide feed to the stripper will be necessarily reduced as compared to a urea plant operating on a stand-alone basis, i.e., without being integrated with the production of melamine. This results in a less efficient operation of the stripper. Whilst this could be offset by increasing the stripping temperature, the latter results in a higher overall energy consumption of the plant, typically in the form of a higher steam requirement (steam being used at the shell-side of the stripper to supply heat). Also, adding more heat to the stripper can only be done by increasing the stripper temperature. However this is limited because higher temperatures decrease the corrosion resistance of the materials from which such strippers are generally fabricated. Accordingly, increasing the stripper temperature increases corrosion, which may cause damage to said stripper, thereby reducing the lifetime thereof.

The invention seeks to provide integrated urea and ammonia production allowing stripping efficiency, steam consumption, or both, to be optimized.

This has not been adequately addressed in the art, despite a vast number of disclosures regarding various ways of integrating the production of urea and melamine. As examples reflecting the state of the art, reference is made to the following documents.

In WO98/08808 A1 a process for the integrated production of urea and melamine is illustrated in the block diagram as given in FIG. 2. In the known process, a gas stream originating from a high pressure process for the preparation of melamine is supplied directly to a high pressure section of a stripping process for the preparation of urea. A disadvantage of the known method is that stable operation of the resulting combined process for the preparation of melamine and urea is difficult: pressure fluctuations in one of the processes can easily affect the other process via the gas stream and thus result in unstable operation and process disorder. Another disadvantage is that the best operation of the known method is achieved if the melamine process has a higher pressure than said high pressure section of the urea process. As mentioned the energy consumption of the urea plant that processes the off-gas of an integrated melamine process increases in relation to a stand-alone urea plant. More specifically, as explained above, the energy consumption increases if the urea plant is a carbon dioxide or ammonia stripping plant type.

Another method is disclosed in U.S. Pat. No. 7,893,298 B2 and is illustrated in the block diagram as given in FIG. 4. In the known process, a gas stream originating from a high pressure process for the preparation of melamine is condensed in an aqueous ammonium carbamate stream that has been formed in a $CO_2$ stripping process for the preparation of urea.

Yet another method is disclosed in WO 2008/052640 A1. In this known process the urea plant contains a medium pressure treatment section including a decomposer. A gas stream from melamine production is fed, together with vapor as formed in said decomposer and with the aqueous ammonium carbamate solution as formed in a downstream urea recovery section, to a condenser of the medium pressure treatment section. This results in a concentrated aqueous carbamate solution that is recycled to the high pressure urea synthesis section.

The invention seeks to reduce the steam consumption of a urea plant, after being integrated with a melamine plant. Alternatively, the invention seeks to keep the steam consumption for the urea production section in an integrated urea and melamine plant at least equal. All in all, the invention thus seeks to increase the economics and functionality in a facility for the integrated production of urea and melamine.

SUMMARY OF THE INVENTION

In order to better address one or more of the foregoing desires, the invention, in one aspect, provides a process for the integrated production of urea and melamine, the process comprising subjecting carbon dioxide and ammonia to urea forming conditions in a urea production zone, so as to form a urea synthesis stream comprising urea, water and ammonium carbamate; subjecting the urea synthesis stream to processing so as to obtain an aqueous urea stream and a vapor comprising ammonia, carbon dioxide, and water; feeding urea to a melamine production zone; subjecting the urea fed to the melamine production zone to melamine forming conditions so as to form melamine and melamine off-gas comprising carbon dioxide and ammonia; feeding the off-gas to the urea production zone; subjecting the vapor and the melamine off-gas to condensation; forming a combined stream of the condensate of the vapor and the condensate of the off-gas, so as to provide a dilute melamine off-gas condensate, and using said dilute melamine off-gas condensate as a fluid in indirect heat-exchange.

The invention also provides a facility for the integrated production of urea and melamine, said facility comprising a urea production zone and a melamine production zone; the urea production zone comprising a urea synthesis section and a carbamate recirculation section comprising a liquid/gas separation section; the melamine production zone comprising a melamine synthesis section and an off-gas separation section; said facility comprising a fluid transport line from the urea production zone to the melamine production zone, said line being suitable for feeding formed urea to the melamine synthesis section, a gas flow line from the off-gas separation section of the melamine production zone to the urea synthesis section, said gas flow line being in communication with a gas inlet of a condenser for melamine off-gas, said condenser comprising a liquid outlet for condensed gas, and a gas flow-line from the liquid/gas separation section in fluid communication with a condenser for vapor comprising ammonia, carbon dioxide, and water, said condenser comprising a liquid outlet for condensed gas, wherein the condenser for melamine off-gas and the condenser for said vapor are comprised in a condensation system, wherein said liquid outlets are integrated into a single fluid transportation system.

In yet another aspect, the invention provides a method for reducing the energy consumption of a urea production zone of a pre-existing facility for the integrated production of urea and melamine, said facility comprising a urea production zone and a melamine production zone; the urea production zone comprising a urea synthesis section and a carbamate recirculation section comprising a liquid/gas separation section; the melamine production zone comprising a melamine synthesis section and an off-gas separation section, the method comprising adding a concentrator to the urea production zone, said concentrator comprising an evaporation chamber for liquid to be heated and evaporated, said evaporation chamber comprising a gas outlet for evaporated liquid and being in heat-exchanging communication with a chamber for indirect heat exchange; providing a transport line for liquid feed from the liquid/gas separation section of the urea plant to said evaporation chamber; providing a gas flow-line from the liquid/gas separation section of the urea plant to a condensation system, said condensation system comprising a liquid outlet in fluid communication with the chamber for indirect heat exchange; and, providing a gas flow-line from the off-gas separation section of the melamine production zone to the condensation system.

In a further aspect, the invention provides a method of increasing the plant capacity of the melamine production zone of a pre-existing facility for the integrated production of urea and melamine, said facility comprising a urea production zone and a melamine production zone; the urea production zone comprising a urea synthesis section and a carbamate recirculation section comprising a liquid/gas separation section; the melamine production zone comprising a melamine synthesis section and an off-gas separation section, the method comprising expanding the melamine synthesis capacity of the melamine synthesis section; adding a concentrator to the urea production zone, said concentrator comprising an evaporation chamber for liquid to be heated and evaporated, said evaporation chamber comprising a gas outlet for evaporated liquid and being in heat-exchanging communication with a chamber for indirect heat exchange; providing a transport line for liquid feed from the liquid/gas separation section of the urea plant to said evaporation chamber; providing a gas flow-line from the liquid/gas separation section of the urea plant to a condensation system, said condensation system comprising a liquid outlet in fluid communication with the chamber for indirect heat exchange; and, providing a gas flow-line from the off-gas separation section of the melamine production zone to the condensation system.

In a still further aspect, the invention presents the use of the foregoing methods for revamping a facility for the integrated production of urea and melamine.

DETAILED DESCRIPTION OF THE INVENTION

Figure 1:
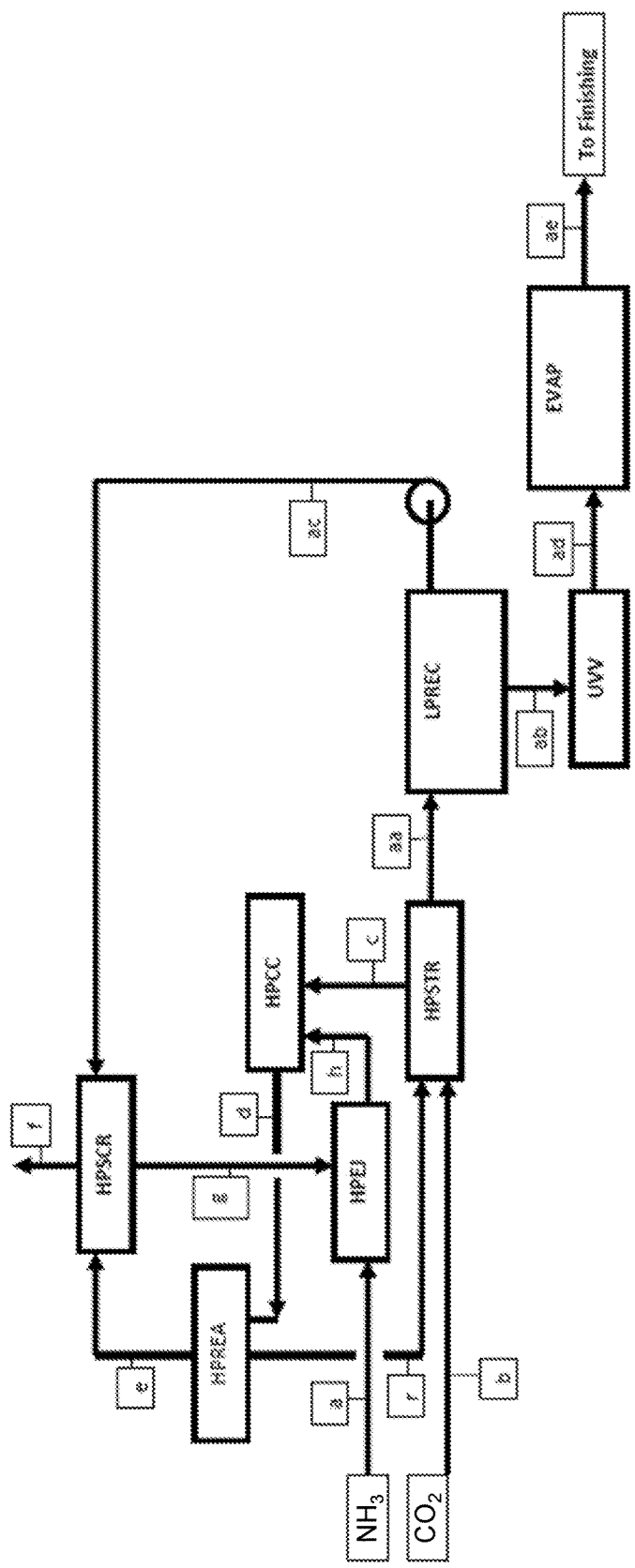
FIG. 1 is a schematic drawing of a conventional urea stripping plant.

In a general sense, the invention is based on the judicious insight how to put to use the thermal energy available from the off-gas stream of a melamine production zone (hereinafter also indicated as melamine off-gas) that is integrated with a urea production zone. This insight has resulted in combining the condensate of said off-gas, which has a relatively low water-content, and that of dissociated carbamate vapor (a gaseous stream comprising ammonia, carbon dioxide, and water) obtained from urea production, and having a higher water-content. The resulting combined condensate has a water-content above that of the off-gas of the melamine production zone. By thus diluting the melamine off-gas upon condensation, the resulting dilute condensate can be put to further use by being transported to elsewhere in the integrated production facility, particularly by being recirculated for use in urea synthesis.

In order to provide the combined condensate, the off-gas of the melamine production zone and the dissociated carbamate vapor of the urea production zone are directed to a condensation system suitable for generating and combining the condensates of both of the gas streams.

Typically, this refers to a system comprising a condenser for melamine off-gas, said condenser comprising a liquid outlet for condensed gas, and a condenser for the dissociated carbamate vapor comprising ammonia, carbon dioxide, and water, said condenser comprising a liquid outlet for condensed gas, wherein said liquid outlets are integrated into a single fluid transportation system. Depending on the relative pressures of the gas streams, as discussed below, the condensation system, can be a single condenser, fed by both of the gas streams. If it is preferred to avoid taking measures to equalize the pressures of both of the gas streams, the condensation system preferably comprises a plurality of condensers in fluid communication with each other.

Essentially, the liquid output of the condensation system is a combined condensate of the off-gas of the melamine production zone and the dissociated carbamate vapor of the urea production zone. In the event that the condensation of both streams does not take place at about the same time or in the same vessel, but in series, it is preferred that the condensation of the melamine off-gas takes place downstream of the condensation of the dissociated carbamate vapor. This way, the condensate of low water-content (viz., that of the melamine off-gas) will be immediately taken up into an aqueous stream, and thus become diluted, so as to prevent the melamine off-gas condensate from solidifying. Preferably, the dilute condensate contains between 20 and 35% by weight of water.

Preferably, the condensation system is provided in the form of the shell side of a shell-and-tube heat exchanger. At any rate, the condensation system is in heat-exchanging communication with a device wherein the heat of condensation is put to use.

In a preferred embodiment of the process according to the invention, the combined condensation of the dissociated carbamate vapor and the melamine off-gas is conducted in an indirect heat exchange with the aqueous urea stream.

Preferably, the indirect heat exchange is carried out in a shell and tube heat exchanger such that the dissociated carbamate vapor and the melamine off-gas are fed to the shell side of the heat exchanger, and the aqueous urea solution to the tube side thereof.

The heat exchange with the aqueous urea stream is employed so as to concentrate said stream. This results in a liquid stream, being a concentrated urea solution, and a gas stream, being evaporated water comprising ammonia and carbon dioxide.

As a result of the invention, the energy consumption of the integrated production facility is improved. More particularly, in the event of the urea production zone being a urea stripping plant, the increase in specific steam consumption in the urea plant is reduced, despite the additional steam needed as a result of the above-discussed lower stripping efficiency in a urea plant that processes off-gas from a melamine plant, and accordingly the amount of carbon dioxide fed directly to the stripper is reduced. Surprisingly the inventors further found that the specific energy consumption even decreases as the melamine production is increased.

It is should be noted that, generally, the off-gas of melamine production will have a pressure in a range of, generally, 1.0-25 MPa, preferably 1.0-3.0 MPa, e.g. 1.5-2.5 MPa, and typically about 2 MPa. In the context of urea production, this would be considered medium pressure. Urea is typically synthesized at a high pressure, e.g. of 10-25 MPa and preferably 12-22 MPa. This implies that, if the dissociated ammonium dissociated carbamate vapor obtained from a high pressure stripper in a urea production zone, is to be joined with the off-gas from a melamine production zone into a combined condensate, the combined condensate will be formed only after condensation of the two gas streams.

In an interesting embodiment, however, the dissociated carbamate vapor is set to have a pressure sufficiently equal to the pressure of the melamine off-gas to allow combination in the gas phase. In that case, it is possible to subject the vapor and the off-gas to combined condensation. This can be done if the dissociated carbamate vapor has about the right pressure, or is brought to the right pressure.

This can be realized, e.g., in a urea production zone provided with a medium-pressure stage. Such urea production zones are familiar to the skilled person. In the medium pressure stage, whole or part of the urea synthesis solution obtained from the high pressure synthesis section, is subjected to stripping, the output of the medium pressure stage being a stripped aqueous urea solution, and a medium-pressure dissociated carbamate vapor. Urea production zones including a medium pressure stage, typically comprising a medium pressure stripper and a medium pressure carbamate condenser, are known to the skilled person. See, e.g., Ullmann's Encyclopedia of Industrial Chemistry, Vol 37, (2012) p 657-693.

Medium pressure dissociated carbamate vapor can also be provided via flashing. In a preferred embodiment, the aforementioned processing of the urea synthesis stream so as to separate the aqueous urea stream from residual dissociated carbamate vapor comprising ammonia, carbon dioxide, and water, comprises subjecting the aqueous urea stream to adiabatic flashing, typically to a pressure in between 1.0 and 8.0 MPa and more specifically in between 1.5 and 5.0 MPa. This results in an expansion, causing a large part of ammonia, carbon dioxide and water to be separated, as a vapor, from the urea solution. This separated vapor, i.e. in effect a dissociated carbamate vapor, is of medium pressure, and can be directed to the same condensation system to which also the melamine off-gas is directed. There, the vapor and the off-gas can be combined in the gas-phase, and then subjected to combined condensation. The remaining urea solution is typically still subjected to regular recirculation processing, i.e. to further separate dissociated carbamate vapor from the urea solution. The latter dissociated carbamate vapor is preferably also directed to the aforementioned condensation system. An advantage of the step of adiabatic flashing, is that the heat from the urea synthesis can be recovered when the vapor resulting from the flashing is condensed and used in indirect heat exchange.

The invention finds useful application in an integrated production process for urea and melamine, and in a production facility therefor. It also finds useful application in a method for reducing the energy consumption of a urea production zone in a facility for the integrated production of urea and melamine. A particularly useful application is in increasing the capacity of a melamine plant integrated with a urea plant. In general, the invention provides a method for revamping a facility for the integrated production of urea and melamine.

The process for the integrated production of urea and melamine according to the invention comprises subjecting carbon dioxide and ammonia to urea forming conditions in a urea synthesis section so as to form a urea synthesis stream comprising urea, water and ammonium carbamate. This can be done using standard urea product technology available in the art.

The urea synthesis stream is subjected to processing, so as to separate urea from residual dissociated carbamate vapor comprising ammonia, carbon dioxide, and water. Methods to accomplish this, are well-known the skilled person. Said dissociated carbamate vapor is generally condensed into a carbamate solution, which solution is recirculated to the urea synthesis section. This too, can be accomplished using standard urea production technology available to the skilled person.

Preferably, the processing of the urea synthesis stream comprises subjecting said stream to stripping so as to form a stripped aqueous urea solution. Stripping can be done by providing heat (thermal stripping), or by using a stripping medium, generally a counter-current flow of a stripping gas. In urea production, typically ammonia or carbon dioxide are used as stripping media.

The stripped aqueous urea solution is subjected to a recirculation step wherein remaining ammonium carbamate is separated from urea, so as to form a urea solution and a dissociated carbamate vapor comprising ammonia, carbon dioxide, and water; said dissociated carbamate vapor is condensed into a carbamate solution, which is recirculated to the urea synthesis section.

In the invention, in one embodiment the condensation of the dissociated carbamate vapor is conducted in combination with the condensation of off-gas obtained from the melamine production section, and recirculated to the urea production section as part of the resulting combined condensate. In another embodiment, the dissociated carbamate vapor is condensed first. The condensate is then brought to a suitable pressure, combined with the melamine off-gas, and then the melamine off-gas is condensed. The condensed fluid is used for heat exchange.

In the course of the integrated production of urea and melamine, urea formed in the urea production section is fed, as a starting material, to the melamine synthesis section where it is subjected to melamine-forming conditions. These conditions, and the associated equipment, for the synthesis of melamine are generally available to the skilled person.

Another part of the integration of urea and melamine production concerns the recirculation of the off-gas of the melamine synthesis section, to the urea synthesis section. It will be understood that, in the invention, this recirculation takes place, wholly or partially, after the above-described combined condensation. In other words, the melamine off-gas, after condensation, is recirculated to the urea synthesis section as part of the combined condensate of said off-gas and of dissociated carbamate vapor from urea production, as explained above.

In addition to the above-identified specific requirements for accomplishing the manner in which the melamine off-gas is used for condensation, the integration of the urea and melamine production can generally be accomplished in a manner known to the skilled person. To this extent, many set-ups for the integration of melamine and urea production plants are available in the art.

The integrated production of urea and melamine requires that a urea production zone and a melamine production zone are coupled as explained above. The production zones can be parts of a single, integrated plant. More typically, the production zones are separate plants, generally in a sufficiently close proximity of each other so as to make the integration economically and practically feasible.

The separate urea and melamine plants can be both built as new plants or, either or both of the plants can be pre-existing. If both plants pre-exist in sufficiently close proximity, it would be customary in the art to already have them integrated. However, it is also conceivable that no such integration has taken place, particularly in view of the drawbacks associated with the stripping efficiency of the urea plant outlined above. The invention obviates these drawbacks.

If the plants pre-exist in an integrated way, it is conceivable that the coupling to the urea plant effectively prevents the skilled person from increasing the capacity of the melamine plant, due to the problem of a lower stripping efficiency and/or higher steam consumption resulting from the increased feed of carbon dioxide and ammonia to the urea plant. The invention now solves this problem.

As to the urea production zone, a frequently used process for the preparation of urea according to a stripping process is the carbon dioxide stripping process as for example described in Ullmann's Encyclopedia of Industrial Chemistry, Vol. A27, 1996, pp 333-350. In this process, the synthesis section is followed by one or more recovery sections. The synthesis section comprises a reactor, a stripper, a condenser and a scrubber in which the operating pressure is in between 12 and 20 MPa and preferably in between 13 and 18 MPa. In the synthesis section the urea solution leaving the urea reactor is fed to a stripper in which a large amount of non-converted ammonia and carbon dioxide is separated from the aqueous urea solution. Such a stripper can be a shell and tube heat exchanger in which the urea solution is fed to the top part at the tube side and a carbon dioxide feed to the synthesis is added to the bottom part of the stripper. At the shell side, steam is added to heat the solution. The urea solution leaves the heat exchanger at the bottom part, while the vapor phase leaves the stripper at the top part. The vapor leaving said stripper contains ammonia, carbon dioxide and a small amount of water. Said vapor is condensed in a falling film type heat exchanger or a submerged type of condenser that can be a horizontal type or a vertical type. A horizontal type submerged heat exchanger is described in Ullmann's Encyclopedia of Industrial Chemistry, Vol. A27, 1996, pp 333-350. The heat released by the exothermic carbamate condensation reaction in said condenser is usually used to produce steam that is used in a downstream urea processing section for heating and concentrating the urea solution. Since a certain liquid residence time is created in a submerged type condenser, a part of the urea reaction takes already place in said condenser. The formed solution, containing condensed ammonia, carbon dioxide, water and urea together with the non-condensed ammonia, carbon dioxide and inert vapor is sent to the reactor. In the reactor the above mentioned reaction from carbamate to urea approaches the equilibrium. The ammonia to carbon dioxide molar ratio in the urea solution leaving the reactor is generally in between 2.5 and 4 mol/mol. It is also possible that the condenser and the reactor are combined in one piece of equipment. An example of this piece of equipment as described in Ullmann's Encyclopedia of Industrial Chemistry, Vol. A27, 1996, pp 333-350. The formed urea solution leaving the urea reactor is supplied to the stripper and the inert vapor containing non-condensed ammonia and carbon dioxide is sent to a scrubbing section operating at a similar pressure as the reactor. In that scrubbing section the ammonia and carbon dioxide is scrubbed from the inert vapor. The formed carbamate solution from the downstream recovery system is used as absorbent in that scrubbing section. In the invention, the formed carbamate in the combined condensate can be sent to the mentioned scrubber as absorbent and/or to the condensation zone in the synthesis section.

The invention is not limited to any particular urea production process. Other processes and plants include those that are based on technology such as the HEC process developed by Urea Casale, the ACES process developed by Toyo Engineering Corporation and the process developed by Snamprogetti.

As to the melamine production zone, this is preferably a melamine plant using a so-called high-pressure process. Melamine production processes are described for example in Ullmann's Encyclopedia of Industrial Chemistry, Vol. A16, fifth ed., pp. 174-179.

The invention also pertains to a facility for the integrated production of urea and melamine. Said facility comprises urea production zone and a melamine production zone, which can take the form of an integrated plant, or of two coupled separate plants, as substantially explained above. The urea production zone comprises a urea synthesis section and a carbamate recirculation section comprising a liquid/gas separation system; the melamine production zone comprises a melamine synthesis section and an off-gas separation section. In order for the production of urea and melamine to be integrated, the facility comprises a fluid transport line from the urea production zone to the melamine production zone, said line being suitable for feeding formed urea to the melamine synthesis section, and a gas flow line from the off-gas separation section of the melamine production zone to the urea synthesis section. In accordance with the invention, the facility further comprises a gas flow-line from the liquid/gas separation system to a condenser.

The aforementioned gas flow line from the melamine off-gas separation section, is directed to the gas inlet of a condenser for said melamine off-gas. The condenser comprises a liquid outlet for condensed gas. The gas flow-line from the liquid/gas separation section of the urea production zone is directed to the gas inlet of a condenser for vapor comprising ammonia, carbon dioxide, and water, said condenser also comprising a liquid outlet for condensed gas. In accordance with the invention, the condenser for melamine off-gas and the condenser for said vapor are comprised in a condensation system, wherein said liquid outlets are integrated into a single fluid transportation system. As will be understood from the above, the condensation system may comprise a single condenser (wherein the gas inlets for both streams may be different, or they may be the same if the gas streams are combined in a location upstream of the condenser), or it may comprise two or more condensers, so as to separately condense the gas streams and then combine the condensates.

Said condensation system preferably comprises the shell-side of one or more shell-and-tube heat-exchangers.

In a preferred embodiment, the urea production zone is based on stripping technology, i.e. a urea stripping plant. The synthesis section of such a plant comprises a reactor and a stripper. In a further preferred embodiment, preferably combined with the aforementioned stripping technology, the condensation zone is in indirect heat exchange with the aqueous urea stream.

Preferably the indirect heat exchange is carried out in a shell and tube heat exchanger, the dissociated carbamate vapor and the melamine off-gas being fed to the shell side of the heat exchanger, and the aqueous urea solution to the tube side thereof.

It will be understood, that, in a preferred embodiment, the condensation system thus is part of a concentrator. From the aqueous urea stream fed into said concentrator, water will evaporate, resulting in a concentrated urea solution, and steam.

With a view of the preferred use, viz. to concentrate an aqueous urea solution, the condensation system preferably comprises one or more liquid feed lines that are in fluid communication with the urea synthesis section. Preferably, at least part of said fluid communication runs via the liquid/gas separation system. In a further preferred embodiment, the urea production zone further comprises a flashing system between the urea synthesis section and the carbamate recirculation section. The flashing system is in fluid communication with the urea synthesis section, so as to allow a urea synthesis stream to be fed to a liquid inlet of the flashing system. The flashing system has a gas outlet allowing dissociated carbamate vapor that is separated out of the urea synthesis stream as a result of flashing, to leave the flashing system. Preferably, said gas outlet is, or comprises, a gas-flow line to the same condensation system to which the melamine off-gas is directed. The flashing system has a liquid outlet that is in fluid communication with the carbamate recirculation section, so as to allow the urea solution remaining after flashing to be directed to the recirculation section, particularly to the liquid/gas separation system thereof.

Flashing systems are known to the skilled person.

The invention further provides a method for reducing the energy consumption of a urea production zone of a pre-existing facility for the integrated production of urea and melamine. The facility comprises a urea production zone and a melamine production zone; the urea production zone comprises a urea synthesis section and a carbamate recirculation section comprising a liquid/gas separation section; the melamine production zone comprises a melamine synthesis section and an off-gas separation section. According to the invention, in one embodiment, the method comprises adding a concentrator to the urea production zone, said concentrator comprising a system for indirect heat-exchange with a gas-stream. The concentrator typically comprises an evaporation chamber for liquid to be heated, said evaporation chamber being in heat-exchanging communication with an indirect heating chamber for heating fluid. The method of the invention further comprises providing a transport line for liquid feed from the liquid/gas separation section of the urea plant to said evaporation chamber. Further, a gas flow-line is provided from the liquid/gas separation section of the urea plant to a condensation system, said condensation system comprising a liquid outlet in fluid communication with the indirect heating chamber. Finally, the invention comprises providing a gas flow-line from the off-gas separation section of the melamine production zone to the condensation system.

A particularly beneficial use of the invention, is in realizing a method of increasing the plant capacity of the melamine production zone of a pre-existing facility for the integrated production of urea and melamine. It will be understood that said facility comprises a urea production zone and a melamine production zone; the urea production zone comprising a urea synthesis section and a carbamate recirculation section comprising a liquid/gas separation section; the melamine production zone comprising a melamine synthesis section and an off-gas separation section. The method of the invention comprises expanding the melamine synthesis capacity of the melamine synthesis section. This can be done in known ways, e.g. by enlarging the size of the melamine reactor and downstream equipment, or by changing the operating conditions so as to allow a larger feed of urea to be processed per unit of time. The invention comprises adding a concentrator to the urea production zone, said concentrator comprising an evaporation chamber for liquid to be heated, said evaporation chamber being in heat-exchanging communication with an indirect heating chamber for heating fluid. The invention further comprises providing a transport line for liquid feed from the liquid/gas separation section of the urea plant to said evaporation chamber and providing a gas flow-line from the liquid/gas separation section of the urea plant to a condensation system. The condensation system comprises a liquid outlet in fluid communication with the indirect heating chamber. In accordance with the invention, a gas flow-line is further provided from the off-gas separation section of the melamine production zone to the condensation system.

As a result, the increased output of the melamine production zone, which goes with an increased output of off-gas comprising carbon dioxide and ammonia, can be employed to benefit from the heat of condensation available in said off-gas, as substantially described hereinbefore. Preferably, the urea production zone comprises a urea stripping plant. It will be understood that particular benefits in increasing the melamine production capacity of the invention, are attained in the event that the urea production zone is based on stripping technology. Reference is made to the aforementioned problem of a lower stripping efficiency resulting from the reduced carbon dioxide or ammonia feed to the stripper that is necessitated by the increased feed of reactants from the melamine off-gas. The invention seeks to obviate this problem, by providing an additional source of heat, viz. from the above-described combined condensation of the melamine off-gas and dissociated carbamate vapor.

In general, either or both of the foregoing methods, i.e. for reducing the energy consumption in a urea production zone and increasing the melamine production capacity of a melamine production zone, can be put to use in revamping a facility for the integrated production of urea and melamine.

The invention will hereinafter be further illustrated with reference to the following non-limiting examples. All the examples relate to a urea plant with a capacity of 1900 mt/day.

Example 1 (Reference)

FIG. 1 illustrates a urea plant according a typical $CO_2$ stripping technology as described in the Ullmann's Encyclopedia of Industrial Chemistry, Vol. A27, 1996, pp 333-350. In this process the carbon dioxide used as a feedstock enters the high-pressure stripper HPSTR via line b. In the stripper HPSTR the reactor effluent from the high-pressure reactor HPREA is contacting counter currently with carbon dioxide, causing the ammonia partial pressure to decrease and the carbamate in that solution to decompose. The heat, required for this purpose to complete the carbamate decomposition to the desired efficiency is supplied by passing saturated high pressure steam around the tubes of the high pressure stripper HPSTR. The vapor leaving the stripper HPSTR comprising ammonia, carbon dioxide and a small portion of water is sent via line c to the high-pressure carbamate condenser HPCC. This high-pressure carbamate condenser HPCC can be a falling film type condenser, a kettle type condenser or a submerged type condenser. In the high-pressure carbamate condenser HPCC the released condensation heat is used to produce saturated steam at a pressure in between 0.2 and 0.6 MPa that is used for i.e. heating in the downstream processing of the urea plant. Ammonia as a feedstock is supplied to the high-pressure carbamate condenser HPCC via line a prior to the high-pressure ejector HPEJ where said ammonia is used as driving force to convey the formed carbamate in the high-pressure scrubber HPSCR via line g to said high-pressure carbamate condenser HPCC via line h.

The formed carbamate in the high-pressure carbamate condenser HPCC comprising ammonia, carbon dioxide, water and optionally urea together with the non-condensed vapor leaving said high-pressure carbamate condenser comprising ammonia, carbon dioxide, water, nitrogen, oxygen and low concentrations of other inert components arrive in the high-pressure reactor HPREA under gravity flow via line d. In the high-pressure reactor the remaining conversion of ammonia and carbon dioxide into urea takes place to approach equilibrium. The formed urea solution leaving the high-pressure reactor HPREA comprising urea, ammonia, carbon dioxide, water and small amounts of other components flow via gravity flow to said stripper HPSTR. The inert vapor leaving the high-pressure reactor HPREA via line e comprising non-condensed ammonia, carbon dioxide, nitrogen, oxygen and small amounts of other inert components are supplied to the high-pressure scrubber HPSCR. In the high-pressure scrubber HPSCR the bulk of non-condensed ammonia and carbon dioxide is separated from the inert vapor comprising mainly the components nitrogen and oxygen by contacting the vapor leaving the high-pressure reactor HPREA with a carbamate solution via line ac formed in the downstream processing of the urea plant. Optionally the carbamate solution leaving the high-pressure reactor HPREA is subjected to a condenser at first where after the leaving inert vapor is brought in contact with said carbamate solution from the downstream processing. The formed carbamate in this scrubber HPSCR is sent via line g to the high-pressure ejector HPEJ. The inert vapor leaving the high-pressure scrubber HPSCR via line f is vented into the atmosphere or is further treated in i.e. an absorber before it is released into the atmosphere.

The urea solution leaving the high-pressure stripper HPSTR is sent to a recirculation section LPREC via line aa. The recirculation section LPREC is operated at a pressure below the pressure in the synthesis section. In this recirculation section LPREC the separation between the non-converted ammonia and carbon dioxide and urea water solution takes place. The separated ammonia and carbon dioxide is condensed to form a carbamate solution that is returned via line ac to the high-pressure scrubber HPSCR in the synthesis section. The urea solution comprising urea, water and small amounts of ammonia and carbon dioxide is collected in a storage tank UVV where after this solution via line ad is concentrated by evaporation EVAP to its desired concentration needed to finish the product via line ae to its final solid product. The energy consumption expressed in kg steam per ton of produced urea varies typically in between 870 and 950 kg per ton depend from the steam quality and type of finishing that is used to produce the final product. In this example the energy consumption is 920 kg/ton.

Example 2 (Reference)

Figure 2:
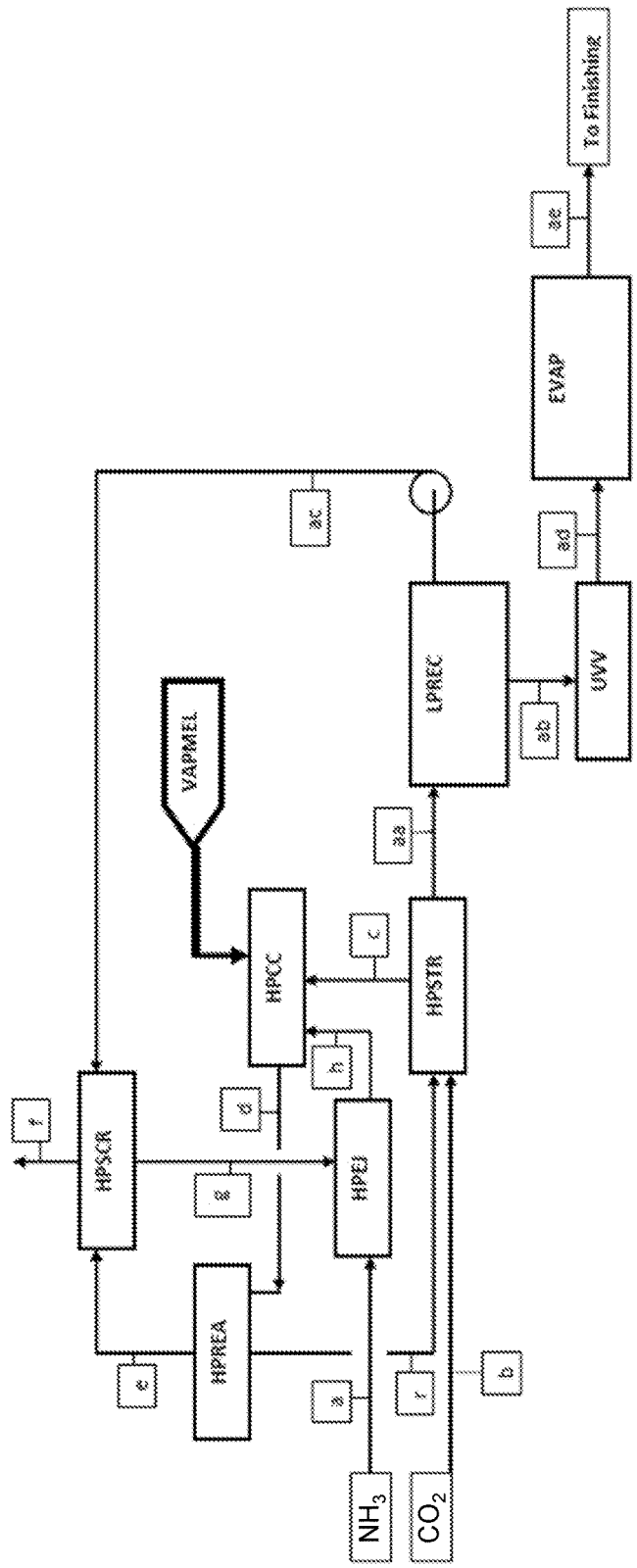
FIG. 2 is a schematic drawing of a facility for the integrated production of urea and melamine according to an embodiment known in the art.

FIG. 2 illustrates the process as described in the prior art and disclosed in WO 98/08808 A1.

This process comprises the urea plant as described for FIG. 1 (capacity 1900 mt/day) and the vapor from the melamine plant comprising ammonia, carbon dioxide and optionally water and inert VAPMEL is added to the high-pressure carbamate condenser HPCC in the synthesis section.

Figure 3:
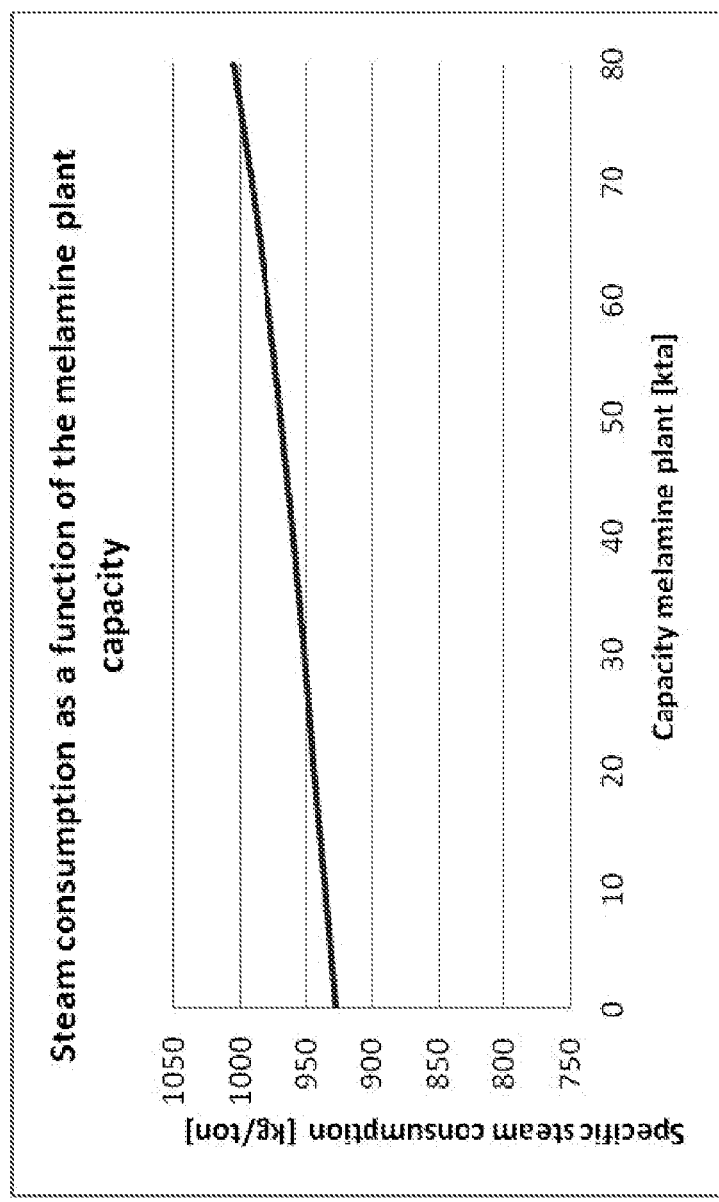
FIG. 3 is a graph wherein a typical energy consumption expressed in kg steam per produced ton of urea product is given as a function of the production capacity of the attached melamine plant at constant urea production capacity, for the embodiment of FIG. 2.

FIG. 3 is a graph wherein a typical energy consumption expressed in kg steam per produced ton of urea product is given as a function of the attached plant capacity of the melamine plant at constant urea production capacity.

As expected, the energy consumption of the urea plant increases if the plant capacity of the connected melamine plant increases caused by the increased vapor from said melamine plant to be processed in said urea plant.

Example 3 (Reference)

Figure 4:
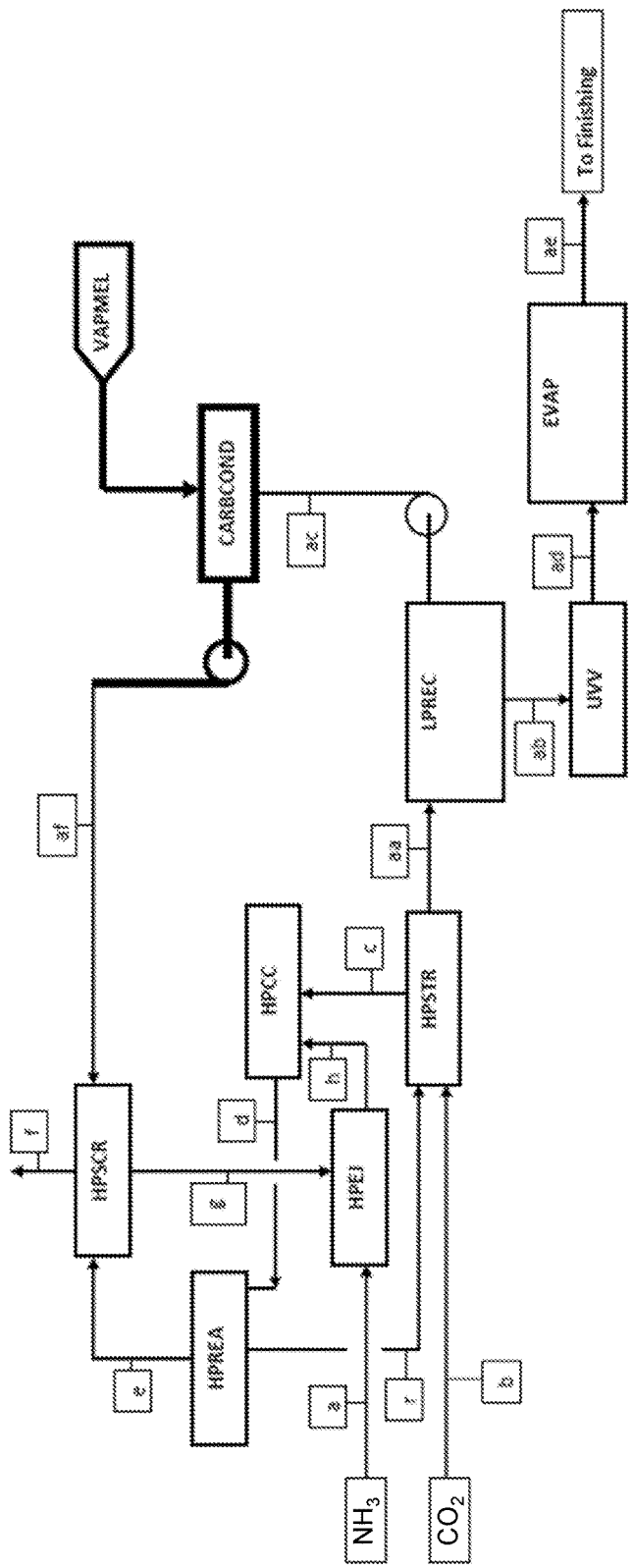
FIG. 4 is a schematic drawing of a facility for the integrated production of urea and melamine according to another embodiment known in the art.

FIG. 4 illustrates an example of an embodiment according the prior art as disclosed in U.S. Pat. No. 7,893,298 B2. This process comprises the urea plant as described for FIG. 1 (capacity 1900 mt/day) and the vapor from the melamine plant comprising ammonia, carbon dioxide and optionally water and inert VAPMEL is condensed in condenser CARBCOND where after the formed carbamate solution is added to the synthesis section of said urea plant. In this example said formed carbamate is added via line of to the high-pressure scrubber HPSCR of the urea synthesis however it is also possible to add this carbamate solution or part of the solution elsewhere in the urea synthesis section such as the high-pressure carbamate condenser HPCC of the urea plant. In the condenser CARBCOND typically the formed carbamate in the downstream processing of the urea plant is added as a solvent via ac and typically the water concentration in said added carbamate solution from the recirculation section LPREC is higher than the water concentration in the formed carbamate solution leaving the condenser CARBCOND. Typically the pressure in the condenser CARBCOND is higher than the pressure in the recirculation section LPREC from which the carbamate is added and lower than the pressure from the melamine plant section where the vapor from the melamine plant VAPMEL is released. In the condenser CARBCOND, the released heat of condensation is dissipated in cooling water or is used to generate steam that might be used in the downstream processing of the urea plant.

Figure 5:
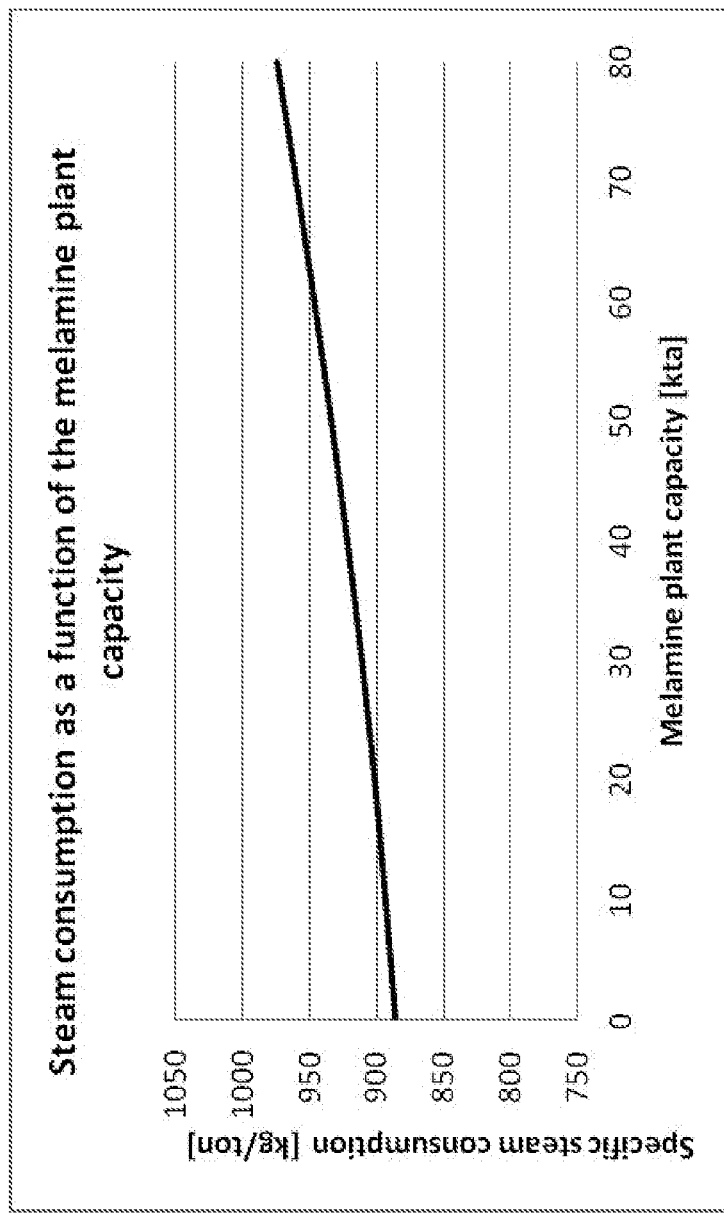
FIG. 5 is a graph as in FIG. 3, for the embodiment of FIG. 4.

FIG. 5 is a graph wherein a typical energy consumption expressed in kg steam per produced ton of urea product is given as a function of the attached plant capacity of the melamine plant at constant urea production capacity. The energy consumption of an integrated urea plant and melamine plant at constant urea production capacity shows that there a slight increase related to the original urea plant without melamine integration.

Example 4

Figure 6:
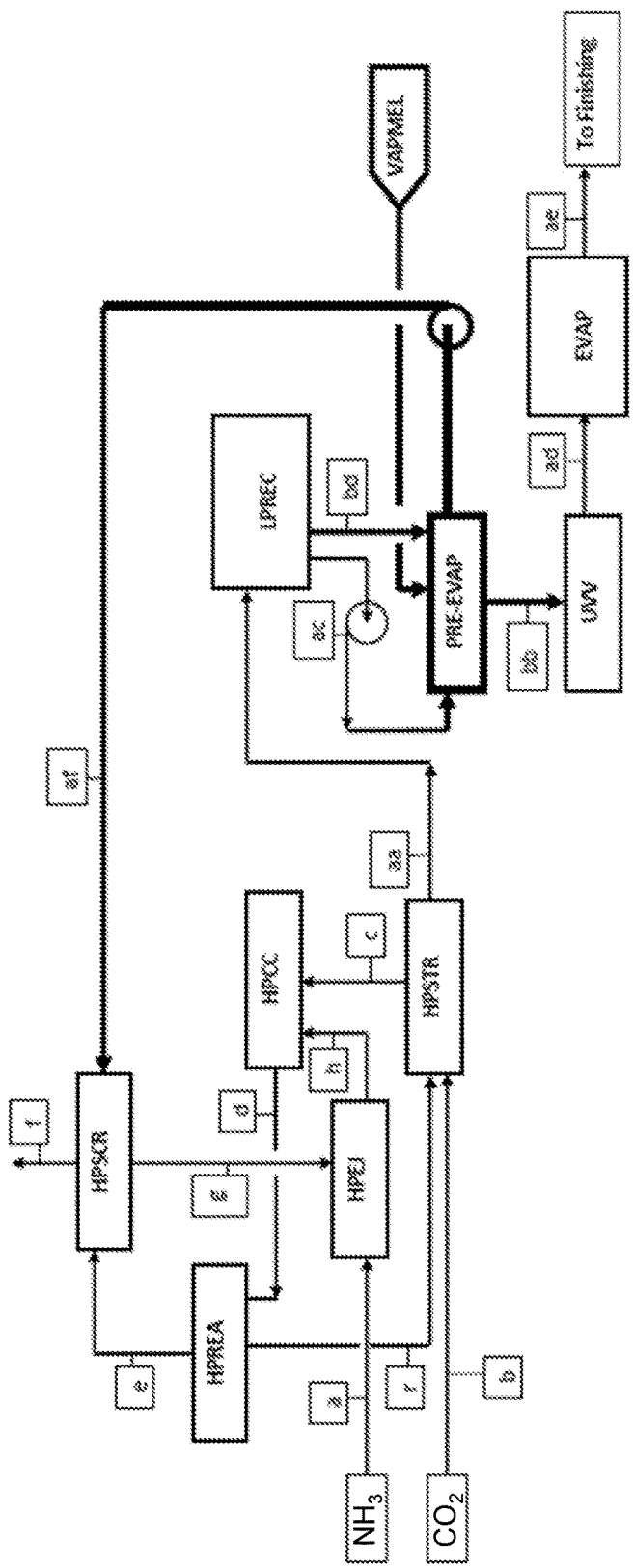
FIG. 6 is a schematic drawing of a facility for the integrated production of urea and melamine according to an embodiment of the invention.

In FIG. 6 a plant and a method according to the invention is elucidated. This process comprises the urea plant as described for FIG. 1 (1900 mt/day). The urea solution leaving the high pressure stripper HPSTR in the synthesis section of the urea plant via line aa is added to the low pressure recirculation. The vapor from the melamine plant comprising ammonia, carbon dioxide and but not necessarily water, is added to a concentrator PREEVAP in which the urea solution leaving the recirculation LPREC via line bd is concentrated where after the concentrated solution is collected in the storage UVV via line bb.

The concentrator PREEVAP is preferably a shell and tube heat exchanger in which the vapors leaving the melamine plant are preferably added to the shell side of this concentrator and the urea solution leaving the recirculation section is preferably added to the tube side of said concentrator. Furthermore the formed carbamate solution produced in the recirculation section is added via line ac to the shell side of the concentrator PREEVAP as well. The formed carbamate in said concentrator PREEVAP is conveyed by preferably a pump via line of to the synthesis section. In this example this carbamate solution is added to the scrubber HPSCR in the synthesis section but elsewhere in the synthesis section such as the high-pressure carbamate condenser HPCC is possible as well. The non-condensed vapor leaving the shell side of this concentrator is usually sent to an absorber placed in the urea plant. Typically the water concentration in said added carbamate solution from the recirculation section LPREC is higher than the water concentration in the formed carbamate solution leaving the concentrator PREEVAP. Typically the pressure in the shell side of the concentrator PREEVAP condenser is equal or below the operating pressure from the vapors added from the melamine plant VAPMEL but higher than the pressure in the low pressure recirculation section LPREC.

Figure 7:
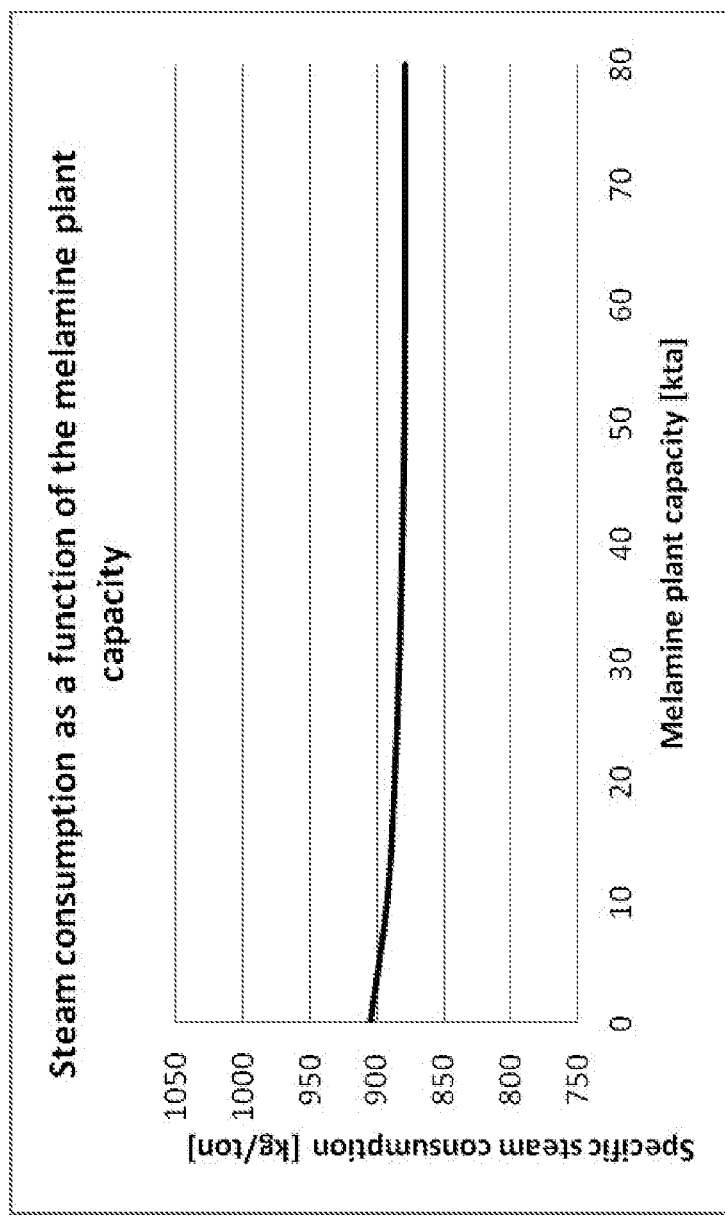
FIG. 7 is a graph as in FIG. 3, for the embodiment of FIG. 6.

FIG. 7 is a graph wherein a typical energy consumption expressed in kg steam per produced ton of urea product is given as a function of the attached plant capacity of the melamine plant at constant urea production capacity.

This graph shows that the energy consumption of an integrated urea plant and melamine plant at constant urea production capacity is about 20 to 50 kg steam per ton of produced urea product lower as compared to a typical urea plant without a melamine integration as shown in FIG. 1. Furthermore the steam consumption of the urea plant at constant production rate decreases at increasing melamine plant capacity.

Example 5

Figure 8:
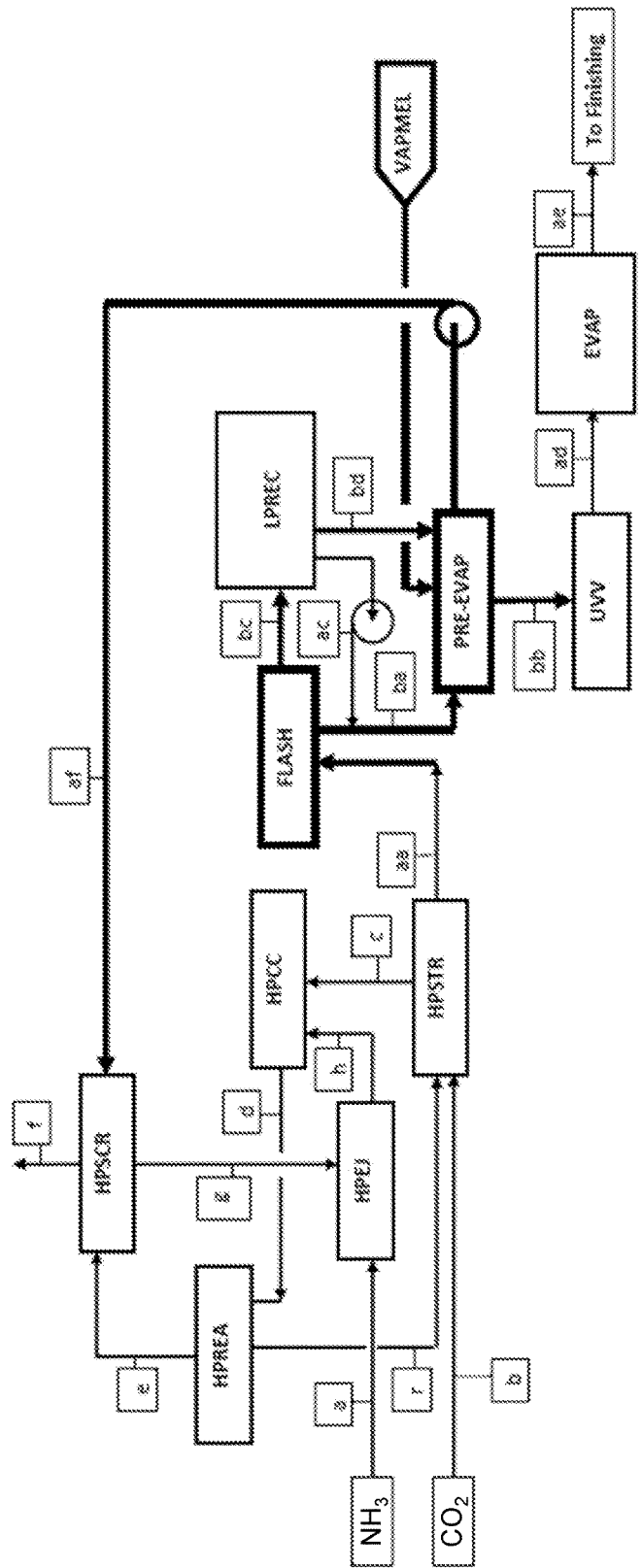
FIG. 8 is a schematic drawing of a facility for the integrated production of urea and melamine according to another embodiment of the invention.

In FIG. 8 another embodiment of the invention is elucidated. This process comprises the urea plant as described for FIG. 1 (capacity 1900 mt/day). The urea solution leaving the high pressure stripper HPSTR in the synthesis section of the urea plant via line aa is adiabatic expanded FLASH to a pressure in between 1.0 and 8.0 MPa and more specifically in between 1.5 and 6.0 MPa. By the expansion a large part of ammonia, carbon dioxide and water is separated from the urea solution that comprises mainly the components urea and water next to some residual ammonia and carbon dioxide that is dissolved in the urea solution. Said urea solution is discharged via line be to the recirculation section LPREC of the urea plant. The flashed vapor from the adiabatic flash step FLASH, comprising ammonia, carbon dioxide and water is discharged via line ba to a concentrator PREEVAP in which the urea solution leaving the recirculation LPREC via line bd is concentrated where after the concentrated solution is collected in the storage UVV via line bb. The vapor leaving the melamine plant comprising ammonia, carbon dioxide and optionally water is added to the concentrator PREEVAP as well. Again the concentrator PREEVAP is preferably a shell and tube heat exchanger in which the vapors leaving the adiabatic expansion FLASH and the vapors leaving the melamine plant are preferably in combination added to the shell side of this concentrator and the urea solution leaving the recirculation section is preferably added to the tube side of said concentrator. Furthermore the formed carbamate solution produced in the recirculation section LPREC is added via line ac to the shell side of the concentrator PREEVAP as well. The formed carbamate in said concentrator PREEVAP is conveyed by preferably a pump via line of to the synthesis section. In this example this carbamate solution is added to the scrubber HPSCR in the synthesis section but elsewhere in the synthesis section such as the high-pressure carbamate condenser HPCC is possible as well. The non-condensed vapor leaving the shell side of this concentrator is usually sent to an absorber placed in the urea plant. Typically the water concentration in said added carbamate solution from the recirculation section LPREC is higher than the water concentration in the formed carbamate solution leaving the concentrator PREEVAP. Typically the pressure in the shell side of the concentrator PREEVAP condenser is equal or below the operating pressure where the adiabatic expansion FLASH takes place although said pressure is higher than the pressure in the recirculation section LPREC from which the carbamate is added.

Figure 9:
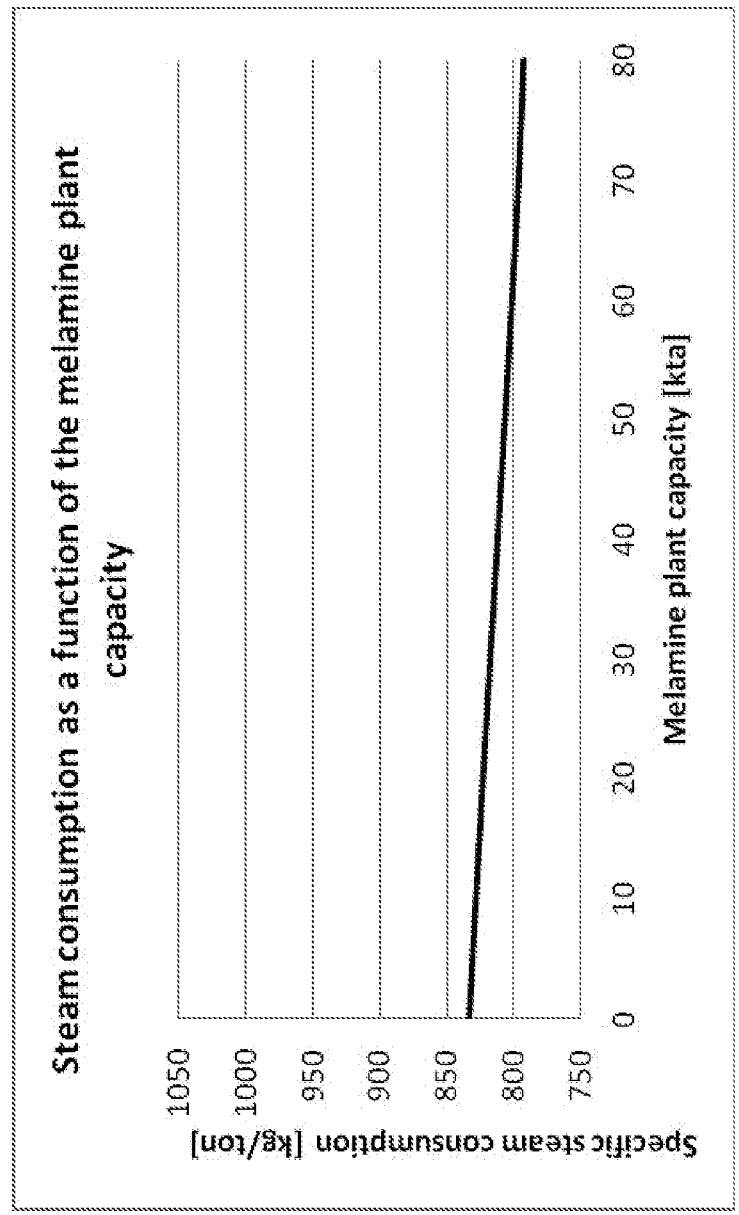
FIG. 9 is a graph as in FIG. 3, for the embodiment of FIG. 8.

FIG. 9 is a graph wherein a typical energy consumption expressed in kg steam per produced ton of urea product is given as a function of the attached plant capacity of the melamine plant at constant urea production capacity.

This graph shows that the energy consumption of an integrated urea plant and melamine plant at constant urea production capacity is about 50 to 150 kg steam per ton of produced urea product lower as compared to a typical urea plant without a melamine integration as shown in FIG. 1. Furthermore the steam consumption of the urea plant at constant rate decreases at increasing plant capacity of the melamine plant.

Example 6

Figure 10:
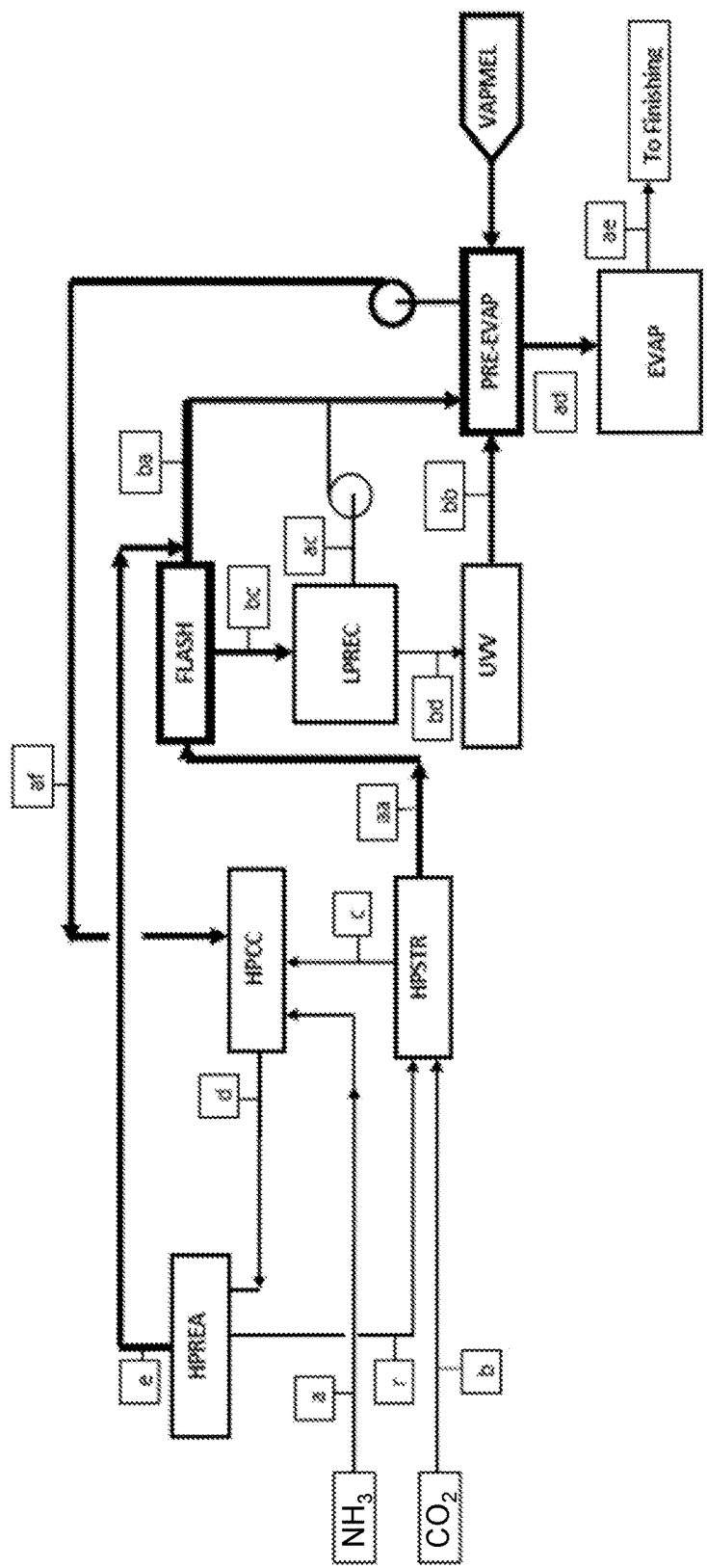
FIG. 10 is a schematic drawing of a facility for the integrated production of urea and melamine according to yet another embodiment of the invention.

This example concerns an embodiment of the invention as shown in FIG. 10. In several aspects, this embodiment is similar to the embodiment as described in Example 5. In the present Example, however, the concentrator PREEVAP is located downstream the storage UVV and upstream the evaporation section EVAP where the urea solution is concentrated to its desired concentration necessary to finish the formed urea melt to its final product. The off-gas leaving the high-pressure reactor in the synthesis section is sent via line e to the flashed vapor from the adiabatic flash FLASH. This embodiment is preferred above the embodiment as shown in FIG. 5 since in this embodiment fuming of ammonia in the storage UVV is avoided and by larger capacities of the melamine plant for instance makes this embodiment possible to concentrate the urea solution in the concentrator PREEVAP deeper without the chance of ammonia fuming in the stored urea solution UVV as compared to the embodiment of Example 5, as shown in FIG. 8.

Figure 11:
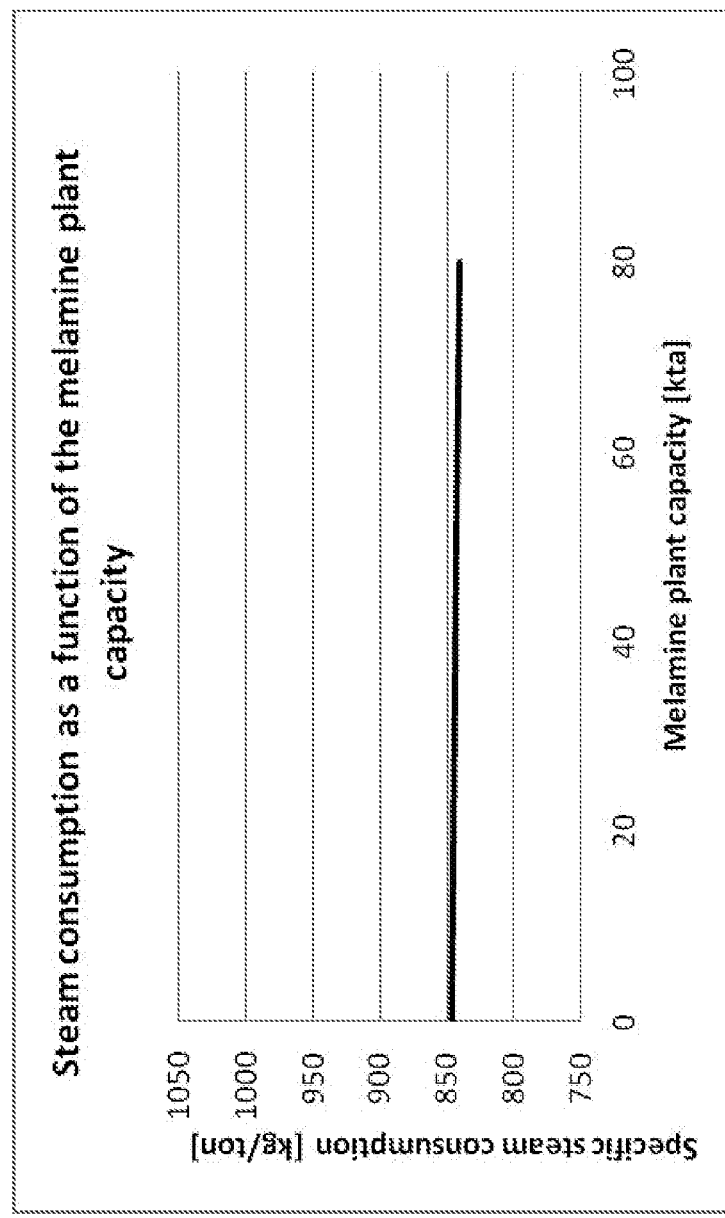
FIG. 11 is a graph as in FIG. 3, for the embodiment of FIG. 10.

FIG. 11 is a graph wherein a typical energy consumption expressed in kg steam per produced ton of urea product is given as a function of the attached plant capacity of the melamine plant at constant urea production capacity.

This graph shows that the energy consumption of an integrated urea plant and melamine plant at constant urea production capacity is about 50 to 150 kg steam per ton of produced urea product lower as compared to a typical urea plant without a melamine integration as shown in FIG. 1. Furthermore the steam consumption of the urea plant at constant rate decreases slightly at increasing plant capacity of the melamine plant.

The invention claimed is:
1. A facility for the integrated production of urea and melamine, said facility comprising a urea production zone and a melamine production zone;

wherein the urea production zone comprises a urea synthesis section, wherein said urea synthesis section comprises a reactor having an outlet for urea-containing solution, and a high pressure stripper for stripping said urea-containing solution, wherein said stripper has an outlet for stripped urea solution, an outlet for gas, and an inlet in fluid communication with said outlet of said reactor, and wherein the urea production zone further comprises a carbamate recirculation section, wherein said carbamate recirculation section comprises an inlet for urea solution and a liquid/gas separation section; and wherein the melamine production zone comprises a melamine synthesis section and an off-gas separation section;

wherein said facility further comprises a first condenser wherein said first condenser comprises an inlet for the off-gases of the melamine production zone and an inlet for gas from the urea production zone, an inlet for liquid, and an outlet for condensate connected with an inlet to the urea synthesis section so as to provide carbamate in to said reactor, wherein said facility further comprises a fluid transport line from the urea production zone to the melamine production zone, said line being suitable for feeding formed urea to the melamine synthesis section, and wherein said facility comprises a gas flow line from the off-gas separation section of the melamine production zone to the gas inlet of said first condenser for said melamine off-gas, and wherein said carbamate recirculation section comprises a gas flow-line from said liquid/gas separation section to an inlet of a second condenser for vapor comprising ammonia, carbon dioxide, and water, wherein said second condenser comprises a liquid outlet for condensate connected with said inlet for liquid of said first condenser; and wherein said urea production zone further comprises a flashing section, wherein said flashing section comprises:
(i) a gas outlet in fluid communication with a gas inlet of said first condenser,
(ii) a liquid outlet in fluid communication with said inlet for urea solution of said carbamate recirculation section; and
(iii) a liquid inlet in fluid communication with said outlet for stripped urea solution of said high pressure stripper.

2. A facility according to claim 1, wherein said facility comprises a urea storage tank having a liquid outlet and a liquid inlet said liquid inlet connected with a liquid outlet of said second condenser, wherein said facility further comprises an evaporation section having an inlet for liquid and an outlet for urea melt, and a shell-and-tube heat exchanger, wherein the first condenser comprises the shell-side of said shell-and-tube heat-exchanger, wherein said shell-and-tube heat exchanger comprises tubes, wherein said tubes have an inlet connected to said liquid outlet of said urea storage tank, and an outlet connected said inlet of said evaporation section.

3. A facility according to claim 1, wherein said urea reactor has an outlet for gas in fluid communication with an inlet for gas of said first condenser.

* * * * *